United States Patent [19]

Underiner

[11] Patent Number: 5,795,897
[45] Date of Patent: Aug. 18, 1998

[54] OXOHEXYL METHYLXANTHINE COMPOUNDS

[75] Inventor: Gail Underiner, Brier, Wash.

[73] Assignee: Cell Therapeutics, Inc., Seattle, Wash.

[21] Appl. No.: 227,295

[22] Filed: Apr. 13, 1994

Related U.S. Application Data

[63] Continuation of Ser. No. 977,993, Nov. 18, 1992.
[51] Int. Cl.$^6$ .................................................. A61K 31/52
[52] U.S. Cl. ............................ 514/261; 514/885; 514/886
[58] Field of Search ................................ 514/261, 885

[56] References Cited

U.S. PATENT DOCUMENTS

| | | |
|---|---|---|
| 3,422,107 | 1/1969 | Mohler et al. . |
| 4,515,795 | 5/1985 | Hinze et al. . |
| 4,576,947 | 3/1986 | Hinze et al. . |
| 4,636,507 | 1/1987 | Kreutzer et al. . |
| 4,965,271 | 10/1990 | Mandell et al. . |
| 4,975,432 | 12/1990 | Weithmann ............................ 514/261 |
| 5,096,906 | 3/1992 | Mandell et al. . |
| 5,118,500 | 6/1992 | Hänel et al. . |
| 5,288,721 | 2/1994 | Klein et al. ............................ 514/263 |
| 5,652,243 | 7/1997 | Bianco et al. ......................... 514/263 |
| B1 3,373,737 | 3/1987 | Mohler et al. . |

FOREIGN PATENT DOCUMENTS

| | | |
|---|---|---|
| 1075690 | 4/1980 | Canada . |
| 03163079 | 7/1991 | Japan . |

OTHER PUBLICATIONS

Davis et al., *Applied Environment. Microbiol.* 48:327, 1984.
Bianco et al., *Blood* 78:1205, 1991.
Singer et al., "Effect of Methylxanthine Derivatives on T cell Activation" *Bone Marrow Transplantation* 10:19, 1992.

Chemical Abstracts An 88–127584 (Dethlefsen et al., May 11, 1988).

J.Pharm. Pharmacol; vol. 44 (11), Issued Nov. 1992, Miyamoto et al, "Selective Bronchodilators from 1–(5'–Oxohexyl)xanthines", pp. 888–892.

Chemical Abstracts 1988: 105950, Wijnandy et al., 1988.

Chemical Abstracts 88–127584, issued 1989, corresponding to DE 3637241 to Dethlefson et al., "Pharmaceutical Compsns. Contg. Nifedipine –and complexing Substance to increase water–solubility". (Abstract only).

Medline Abstract # 88256298 Sullivan et al, "Inhibition of the Inflammatory Action of interleukin–1 and Tumor Necrosis Factor on neutrophil Function by Pentoxifylline", *Infect Immun*, 56(7)1722–9, Jul. 1988.

*Primary Examiner*—Keith MacMillan
*Attorney, Agent, or Firm*—Stephen Faciszewski; Cynthia L. Shumate

[57] ABSTRACT

There is disclosed a pharmaceutical composition comprising 1-(5-oxohexyl)-3-methylxanthine in admixture with a pharmaceutically acceptable excipient, wherein the pharmaceutical composition is useful for treating an immune disorder. There is also disclosed a method to modulate the response of a target cell to a stimulus, which method comprises contacting said cell with an amount of 1-(5-oxohexyl)-3-methylxanthine or a pharmaceutical composition thereof, wherein said amount effects a diminution in elevated levels of unsaturated, non-arachidonate phosphatidic acid (PA) and diacylglycerol (DAG) derived from said PA in said cells wherein said elevated levels are stimulated by an agent capable of elevating levels of said PA and said DAG, said diminution being equal to or greater than the diminution effected by treating said cells with pentoxifylline (PTX) at a concentration of 0.5 mmol, thereby modulating the response of said target cell.

5 Claims, 5 Drawing Sheets

OXOHEXYL METHYLXANTHINE COMPOUNDS

This is a Continuation of U.S. application Ser. No. 07/977,993, filed Nov. 18,1992

TECHNICAL FIELD OF THE INVENTION

The invention relates to a class of substituted oxohexyl methylxanthine compounds that are effective agents to modulate cellular responses to stimuli. More specifically, the inventive relates to a pharmaceutical composition comprising a ketone compound, 1-(5-oxohexyl)-3-methylxanthine and methods of using said ketone for various treatment applications. For example, 1-(5-oxohexyl)-3-methylxanthine is a useful antagonist to control intracellular levels of specific sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,307 and 3,737,433. Metabolites of PTX were summarized in Davis et al., Applied Environment Microbiol. 48:327, 1984. A metabolite of PTX is 1-(5-hydroxyhexyl)-3,7-dimethylxanthine, designated M1. M1 was also disclosed as increasing cerebral blood flow in U.S. Pat. Nos 4,515,795 and 4,576,947. Moreover, 1-(5-oxohexyl)-3-methylxanthine was designated as the M6 metabolite. No activity has been attributed to the M6 metabolite of PTX. In addition, U.S. Pat. Nos. 4,833,146 and 5,039,666 disclose use of tertiary alcohol analogs of xanthine for enhancing cerebral blood flow.

Furthermore, U.S. Pat. No. 4,636,507 describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., Blood 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective uses for the M6 metabolite of PTX and to determine if M6 is an active agent for novel therapeutic indications.

SUMMARY OF THE INVENTION

The invention is directed to the use of 1-(5-oxohexyl)-3-methylxanthine(also referred to as M6 or CT1505 herein) in modulating cellular response to external or in situ primary stimuli, as well as to specific modes of administration of such compounds in effective amounts.

The present invention further comprises a method for modulating an immune response or a cellular response to external or in situ primary stimuli comprising administering an effective amount of 1-(5-oxohexyl)-3-methylxanthine. More specifically, the invention is directed to methods to decrease proliferation of tumor cells in response to an activated oncogene; to stimulate hematopoiesis in the presence of agents which inhibit hematopoiesis, such as chemotherapeutic agents; to suppress the activation of T-cells in the presence of antigen and the secretion of antibodies by B-cells in the presence of antigen; to suppress the activation of macrophage or endothelial cells by endotoxins, TNF, IL-1 or GM-CSF; to enhance the resistance of mesenchymal cells to tumor necrosis factor (TNF); to inhibit the proliferation of smooth muscle cells endothelial cells, fibroblasts and other cell types in response to growth factors, such as PDGF-AA, BB, FGF, EGF, etc.; to inhibit the activation of T-cells and viral replication in response to human immunodeficiency virus; to inhibit the proliferation of kidney mesangial cells in response to IL-1; to prevent suppression of Steel factor (also called stem cell factor, mast cell growth factor and kit ligand), G-CSF, oncostatin M or IL-6 in bone marrow stromal cells in response to TNF; to suppress expression of adhesion molecules in endothelial cells and suppress adhesion of inflammation cells to endothelial cells; to suppress proliferation of kidney mesangial cells in response to IL-1, mip-1α, PDGF or FGF; to prevent toxicity in kidney glomerular or tubular cells in response to cyclosporin A or amphotericin B; to prevent cytotoxic effects in gastrointestinal or pulmonary epithelial cells in response to a cytotoxic drug or radiation; to enhance the antitumor effects in tumor cells in response to a nonalkylating antitumor agent; to suppress the production of metalloproteases in synovial cells, other fibroblasts and a glomerular epithelial cell in response to inflammatory stimuli, such as TNF, IL-1 and the like, to inhibit production of osteoclast-activating factor (OAF) by osteoclasts in response to IL-1; to inhibit degranulation of mast cells and basophils in response to IgE; to modulate signal transduction of the neurotransmitters epinephrine and acetylcholine in neural pathways utilizing these transmitters, block activation of platelet activating factor in inflammation cells, block release of TNF and IL-1 in various cell types in response to inflammatory stimuli, block activation and proliferation of lymphocytes and other cell types to IL-1 and IL-2, and the like including the clinical manifestations of these cellular events, comprising administering a pharmaceutical composition comprising an effective amount of 1-(5-oxohexyl)-3-methylxanthine. Preferably, the pharmaceutical composition further comprises a pharmaceutically acceptable excipient or group of excipients.

In still another aspect, the invention is directed to a pharmaceutical composition comprising 1-(5-oxohexyl)-3-methylxanthine and an effective amount of an agent which reduces the activity of the enzyme P-450, such as a quinolone, to increase the pharmacokinetic half-life of 1-(5-oxohexyl)-3-methylxanthine.

DETAILED DESCRIPTION OF THE INVENTION

Figure 1:
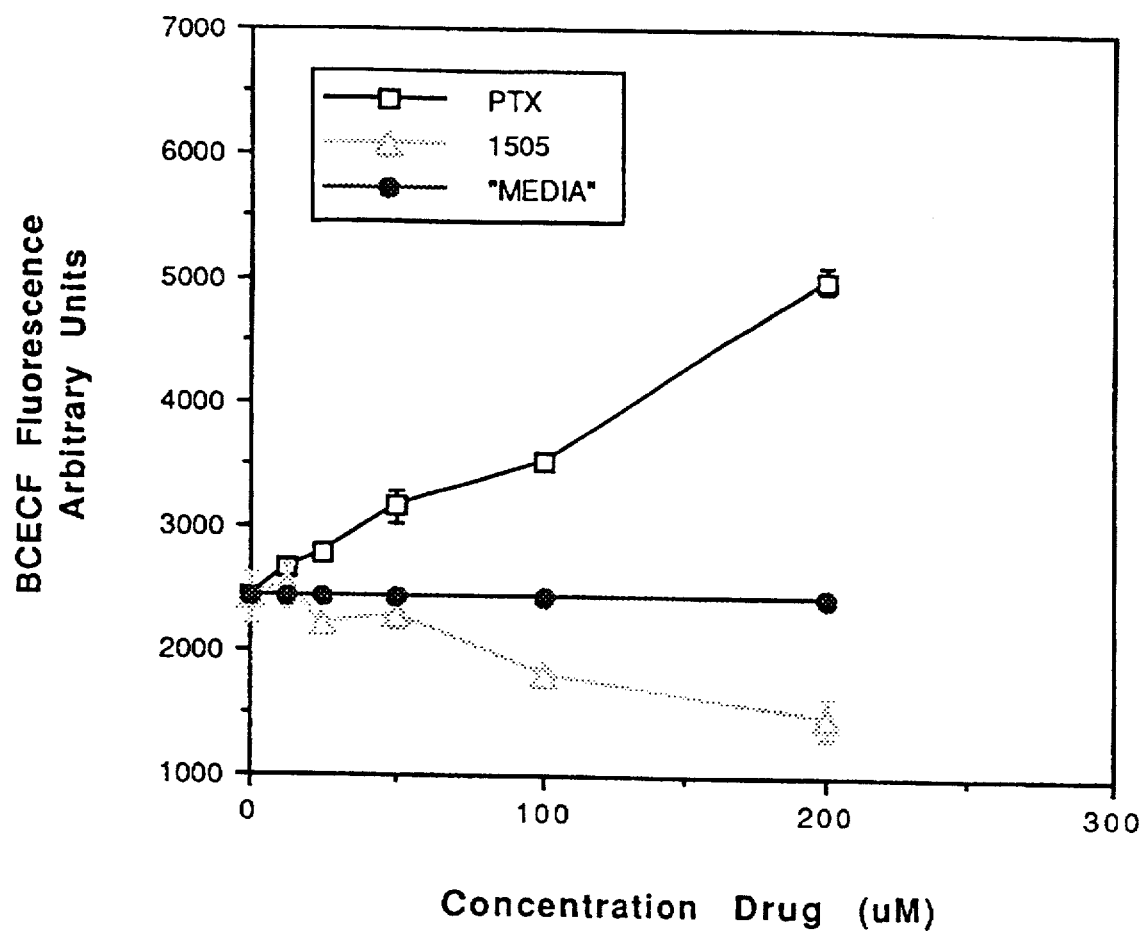
FIG. 1 shows a L929 TNF (tumor necrosis factor) cytotoxicity assay comparing CT 1505 (1-(5-oxohexyl)-3-methylxanthine) with PTX and control (media) at various drug concentrations by measuring cell viability with a fluorescent dye.

The invention is directed to a method of using 1-(5-oxohexyl)-3-methylxanthine which can control cellular behavior by a particular phase of a secondary messenger pathway system (Bursten et al. *J. Biol. Chem.* 266:20732, 1991). It is by inhibiting second messenger signal transduction that CT1505 is able to exhibit therapeutic activity and therapeutic usefulness in a wide range of therapeutic indications, depending upon the cell types affected. The second messengers are lipids or phospholipids and use the following abbreviations:

PE=phosphatidyl ethanolamine

LPE=lysophosphoethanolamine

PA=phosphatidic acid

LPA=lysophosphatidic acid

DAG=diacylglycerol

LPLD=lysophospholipase-D

LPAAT=lysophosphatidic acid acyl transferase

PAPH=phosphatidic acid phosphohydrolase

PLA2=phospholipase A-2.

PLD=phospholipase D

PAA=phosphoarachidonic acid

PLA-2=phospholipase A2

PC=phosphatidyl choline

"remodeled" PA, cyclic pathway=PAA, LPA, PA and DAG intermediates substituted with L-saturated, 2-linoleoyl or 1,2-dileolyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains. "PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as interleukin-1 or TNF) acting at a receptor on a cellular surface. An immediate detectable effect is an elevation of levels of PA and DAG. Administration of CT1505 reverses this elevation.

In Vitro Assays for Physiologic and Pharmacological Effects of 1-(5-oxohexyl)-3-methylxanthine Various in vitro assays can be used to measure effects of 1-(5-oxohexyl)-3methylxanthine to module immune activity and have antitumor activity using a variety of cellular types.

For example, a mixed lymphocyte reaction (MLR) provides a valuable screening tool to determine biological activity of 1-(5-oxohexyl)-3-methylxanthine. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 µl complete medium are co-cultured with approximately $10^5$ autologous (control culture) or allogeneic (stimulated culture) PBMC cells, wherein the allogeneic cells are from HLA disparate individuals. Varying doses of 1-(5-oxohexyl)-3-methylxanthine (drug) are added at the time of addition of cells to the microtiter plate. The cultures are incubated for 6 days at 37° C. in a 5% $CO_2$ atmosphere. At the conclusion of the incubation tritiated thymidine is added (for example, 1 µCi/well of 40 to 60 Ci/mmole) and proliferation determined by liquid scintillation counting.

A thymocyte costimulator assay is conducted to evaluate 1-(5-oxohexyl)-3-methylxanthine to inhibit activation and proliferation of thymocytes caused by stimulation with Con A and interleukin-1 (IL-1), or interleukin-1 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2 \times 10^5$ cells/well) and a stimulating agent, such as Con A, IL-1 (e.g., IL-1α) or IL-2 is added to the well. The cells are incubated for 4 days at 37° C. On the fourth day, the cells are pulsed with tritiated thymidine and cell proliferation determined. 1-(5-oxohexyl)-3-methylxanthine is added at the time of stimulating agent addition.

1-(5-oxohexyl)-3-methylxanthine was investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (2', 7'-bis-(2-carboroxyethyl)-5-(and -6)- carboxyfluorescein acetoxymethyl ester, BCECF excitation 488 nm and emission 525 nm) 24,48 or 72 hours after addition of the drug.

Another assay for measuring activity of 1-(5-oxohexyl)-3-methylxanthine involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of 1-(5-oxohexyl)-3-methylxanthine on inhibiting proliferation of stimulated B-cells, stimulated by an anti-mu antibody (40 µg/ml), IL4 or PMA (2.5 nM). Ramos B-cell tumor cells or murine splenocytes can be incubated with a stimulating agent, 1-(5-oxohexyl)-3-methylxanthine and tritiated thymidine to measure inhibition of cell proliferation caused by the stimulating agent.

Drug inhibitory activity can also be measured by determining levels of vascular cell adhesion molecule (VCAM) in stimulated cells. Early passage human umbilical vein endothelial cells (HUVEC) (obtained from commercial suppliers such as Cell Systems, Inc. or Clonetics) are cultured in media (e.g., Hepes buffered media, Cell Systems) containing 10% fetal bovine serum, and supplemented with a stimulating agent, such as fibroblast growth factor (acidic FGF, Cell Systems, Inc.) or TNF. The cells are plated into wells of a microtiter plate (e.g., $5 \times 10^4$ per well) and allowed to incubate at 37° C. for 72 hrs. The resting cells are removed (e.g., 20–30 min treatment with 0.4% EDTA), washed in media (e.g., phosphate buffered saline plus 0.1% bovine serum albumin with 0.01% sodium azide) and labeled on ice with a monoclonal antibody ("first antibody") recognizing human VCAM (e.g., 1 µg of a murine monoclonal antibody recognizing human VCAM, Genzyme). After 60 min on ice, the cells are washed (preferably twice) with cold wash media and incubated with an antibody that recognizes the first antibody, (e.g., 1 µg of goat anti-mouse IgG conjugated with phycoerythrin, CalTag, Inc.). After 30 min on ice, the cells are washed twice and analyzed on a flow cytometer (COULTER ELITE®) at appropriate emission and excitation wavelengths (e.g., for phycoerythrin use excitation at 488 nm and emission at 525 nm).

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of 1-(5-oxohexyl)-3-methylxanthine at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes or plasma membranes derived as described in Bursten et al. (*J. Biol. Chem.* 226:20732–20743, 1991) detergent-solubilized microsomes; synaptosomes, and membranes or other cell preparations solubilized using, for example, NP-40,Miranal, SDS or other neutral detergents; and detergent-solubilized or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, *Biochemistry* 30:6195–6203, 1991. A Rainin mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

Uses of the Invention Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus.

For example, 1-(5-oxohexyl)-3-methylxanthine is used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. CT1505 is able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation; in addition, GVHD contributes to the death rate in allogeneic marrow recipients.

Other indications for which it is useful to administer CT1505 includes the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, serious drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV1, changes in vital capacity, and extensive mucus production.

Other suitable subjects for the administration of CT1505 includes patients being administered toxic agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

CT1505 is able to decrease enhanced levels of a relevant PA and DAG resulting from stimulation of synaptosomes with acetylcholine and/or epinephrine. This suggests that the effects of CT1505 is to both enhance release of inhibitory neural transmitters such as dopamine, and to modulate distal "slow current" effects of such neurotransmitters.

Thus, 1-(5-oxohexyl)-3-methylxanthine is also useful to raise seizure threshold, to stabilize synapses against neurotoxins such as strichnine, to potentiate an effect of anti-Parkinson drugs such as L-dopa, to potentiate effects of soporific compounds, to relieve motion disorders resulting from administration of tranquilizers, and to diminish or prevent neuron overfiring associated with progressive neural death following cerebral vascular events such as stroke. In addition, CT1505 is useful in the treatment of norepinephrine-deficient depression and depressions associated with the release of endogenous glucocorticoids, to prevent the toxicity to the central nervous system from dexamethasone or methylprednisolone, and to treat chronic pain without addiction to the drug. Further, CT1505 is useful in treating children with learning and attention deficits and generally improves memory in subjects with organic deficits, including Alzheimer's patients.

While dosage values will vary, therapeutic efficacy is achieved when 1-(5-oxohexyl)-3-methylxanthine is administered to a human subject requiring such treatment as an effective oral, parenteral, or intravenous sublethal dose of about 200 mg to about 5000 mg per day, depending upon the weight of the patient. A particularly preferred regimen for use in treating leukemia is 4-50 mg/kg body weight. It is to be understood, however, that for any particular subject, specific dosage regimens should be adjusted to the individual's need and to the professional judgment of the person administering or supervising the administration of 1-(5-oxohexyl)-3-methylxanthine.

The present invention further comprises a pharmaceutical composition comprising 1-(5-oxohexyl)-3-methylxanthine (also called CT1505 or M6 herein) and a pharmaceutically acceptable carrier or excipient. The cells to be treated with an inventive compound or inventive pharmaceutical composition may either be contacted with the compound of the invention in vitro culture, in an extracorporeal treatment, or by administering the compound of the invention or pharmaceutical composition to a subject whose cells are to be treated. Coadministration With a P450 Inhibitor The coadministration in vivo of 1-(5-oxohexyl)-3-methylxanthine along with an inhibitor of P-450 results in an enhanced effect due to a longer half life of the inventive compounds. This in vivo effect is due to inhibition of a degradation pathway for 1-(5oxohexyl)-3-methylxanthine. For example, NIH3T3-D5C3 cells can be used to compare effects of a compound of Formula 1 alone or in combination with a P-450 inhibitor by comparing transformation phenotype control, incubation with 1-(5-oxohexyl)-3methylxanthine alone, and coincubation of 1-(5-oxohexyl)-3-methylxanthine with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

For combination therapy, 1-(5-oxohexyl)-3-methylxanthine and a P-450 inhibitor can be administered individually or in a single composition. A suitable formulation will depend on the nature of the disorder to be treated, the nature of the medicament chosen, and the judgment of the attending physician. In general, 1-(5-oxohexyl)-3-methylxanthine is formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, PA.

The level of dosage of 1-(5-oxohexyl)-3-methylxanthine can be appreciably diminished by coadministration of a P-450 inhibitor, such as the quinolone. Alternatively, a strong synergistic effect may be obtained with such a quinolone.

The invention is illustrated by the following examples which should not be regarded as limiting the invention in any way. In these examples PTX means pentoxifylline.

EXAMPLE 1

This example illustrates a method for synthesis of CT1505 (1-(5-oxohexyl)-3-methylxanthine). A mixture of 3-methylxanthine (1.00 g, 6.0 mmol) and NaH (145 mg, 6.0 mmol) in DMSO (dimethyl sulfoxide) (20 ml) was stirred until homogeneous (about 30 min). Chloromethylpivalate (865 µl, 904 mg, 6.0 mmol) was added and the reaction mixture was stirred for 18 hrs. The reaction mixture was poured into 70 ml of water and extracted with 25% ethanol/dichloromethane (4×60 ml). The combined organic extracts were combined, dried with sodium sulfate, and then evaporated in a rotoevaporator to a volume of 40 ml. The solution was cooled in ice water and it formed a thick, white precipitate. The solid was filtered off under suction and dried under vacuum to give the 3-methyl-7-(methylpivaloyl) xanthine (1.43 g, 5.4 mmol, 90% yield).

3-Methyl-7-(methylpivaloyl)xanthine (406 mg, 1.5 mmol) was added to a stirring suspension of NaH (36 mg, 1.5 mmol) in DMSO (20 ml) and stirred for 15 min. 6-Bromo-2-hexanone (260 mg, 1.5 mmol) was added and the reaction mixture was stirred for 20 hrs. The reaction mixture was poured into 100 ml of water and extracted with 25% ethanol/dichloromethane (3×40 ml). The combined organic extracts were combined, dried with magnesium sulfate and the solvent was removed under vacuum to give a brown oil. The brown oil was chromatographed (10 g silica gel, ethyl acetate) to give 1-(5-oxohexyl)-3-methyl-7-(methylpivaloyl)xanthine (270 mg, 49% yield)

A sodium methanol solution (prepared by adding sodium (20 mg, 0.9 mmol) to 1 ml of methanol) was added to a solution of 1-(5-oxohexyl)-3-methyl-7(methylpivaloyl) xanthine (270 mg, 0.7 mmol) in 4 ml of methanol and stirred for 15 min. The reaction mixture was poured into water (20 ml), then extracted with 25% ethanol/dichloromethane (4×50 ml). The organic extracts were combined, dried with sodium sulfate, and evaporated to give a yellow solid. The solid was washed with ether to remove impurities and give CT1505 (1-(5-oxohexyl)-3-methylxanthine) as a white solid (120 mg, 0.45 mmol, 65% yield).

EXAMPLE 2

This example illustrates antitumor and cytotoxicity activity of CT1505 as measured in several different assay systems. In one assay, CT1505 was assayed for activity protecting TNF-mediated cytotoxicity. In this assay, L929 murine fibroblast cells ($10^4$ cells per well) were incubated with either CT1505 or PTX at varying doses (see FIG. 1) and media control for two hrs. TNF-α (R&D Systems) was added at a concentration of 500 pg/ml, which is four times the LD50 of TNF (125 pg/ml). The cells plus (or minus) drug plus TNF were incubated for 40 hrs at 37° C. The media was removed and replaced with fresh media containing 2% serum and 10 lg/ml of BCECF fluorescent dye and incubated for 30 min. The fluorescent dye-containing media was removed and replaced with PBS (phosphate buffered saline) and each well was assayed for fluorescence.

The results of this experiment are presented in FIG. 1. These data show that CT1505 protected the fibroblast cells from TNF cytotoxicity better than PTX and much better than the control cells. Coupled with data showing cytotoxicity in tumor cells for CT1505, these data show that CT1505 has therapeutic activity for cancer treatment.

EXAMPLE 3

This example illustrates the effects of CT1505 to inhibit adhesion of U937 cells to TNF-activated HUVEC cells In this experiment, HUVEC cells were induced with human TNF-α(20ng/ml) and and incubated with drug (CT1505) at varying concentrations for 14–16 hrs. U937 cells (a human monocyte cell line) were incubated and labeled with BCECF (10 µg/ml), a fluorescent dye. The U937 cell preparation (2.5×104 cells per well) was layered on top of the activated HUVEC cells. The cells were reverse spun to remove partially adhering and nonadhering U937 cell. The adherent U937 cells were measured by fluorescence on a fluorescent plate reader.

Figure 2:
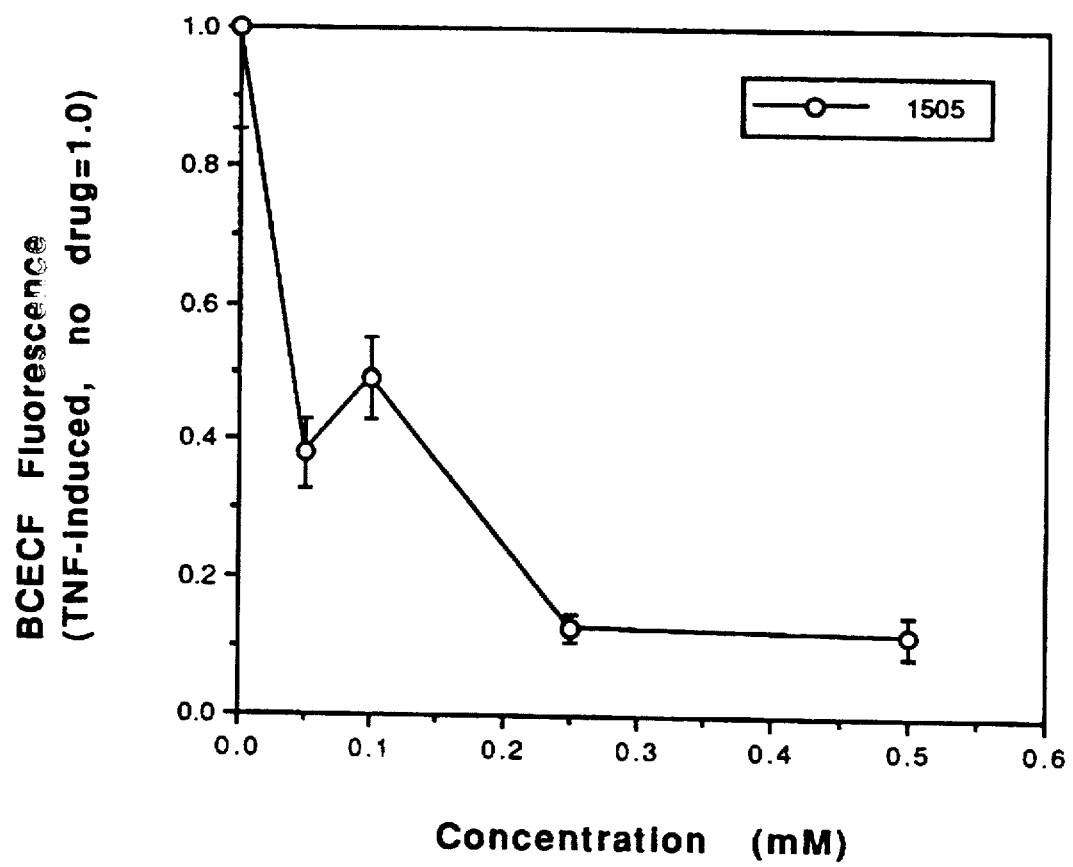
FIG. 2 shows that CT1505 inhibits adhesion of U937 cells to TNF activated human umbilical vein endothelial cells (HUVEC). CT1505 inhibitory activity was noted in the tenths of mM concentration range.

The data for an experiment with varying concentrations of CT1505 is shown in FIG. 2. CT1505 inhibited the inflammatory response of the activated HUVEC cells to adhere U937 monocytes in a dose response fashion. Therefore, CT1505 has antiinflammatory activity as shown by this in vitro assay.

EXAMPLE 4

Figure 3:
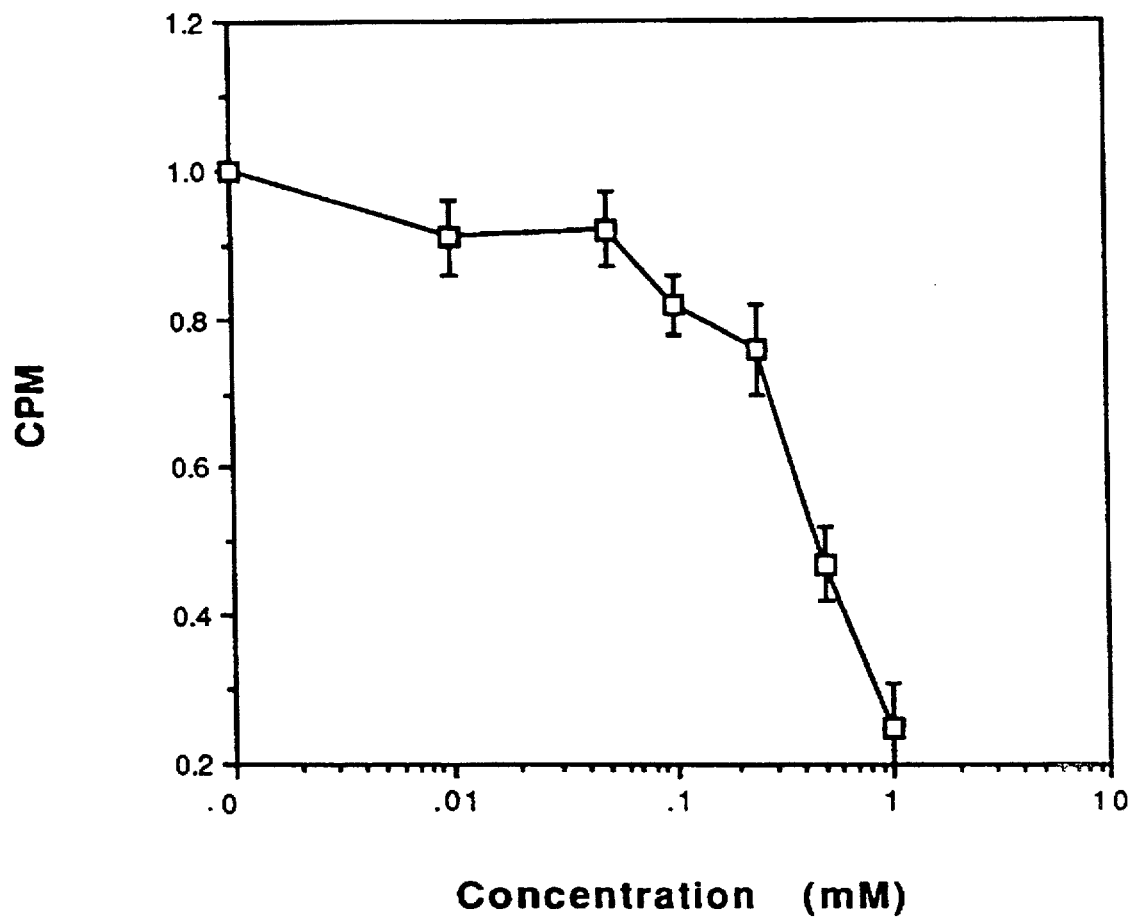
FIG. 3 shows CT1505 cytotoxicity on LD-2 cells, a human malignant melanoma cell line. The cells were treated with various concentrations of CT1505 and later stained for cell viability with a fluorescence stain. CT1505 is cytotoxic at higher concentrations, and thus shows antitumor activity.

This example illustrates that CT1505 has cytotoxic activity for the LD-2 tumor cell line. Cytotoxicity of LD-2 cells was determined with concentrations of CT1505 up to 1.0 mM (see FIG. 3). Cytotoxic activity was seen at drug concentrations over 0.1 mM.

EXAMPLE 5

Figure 4:
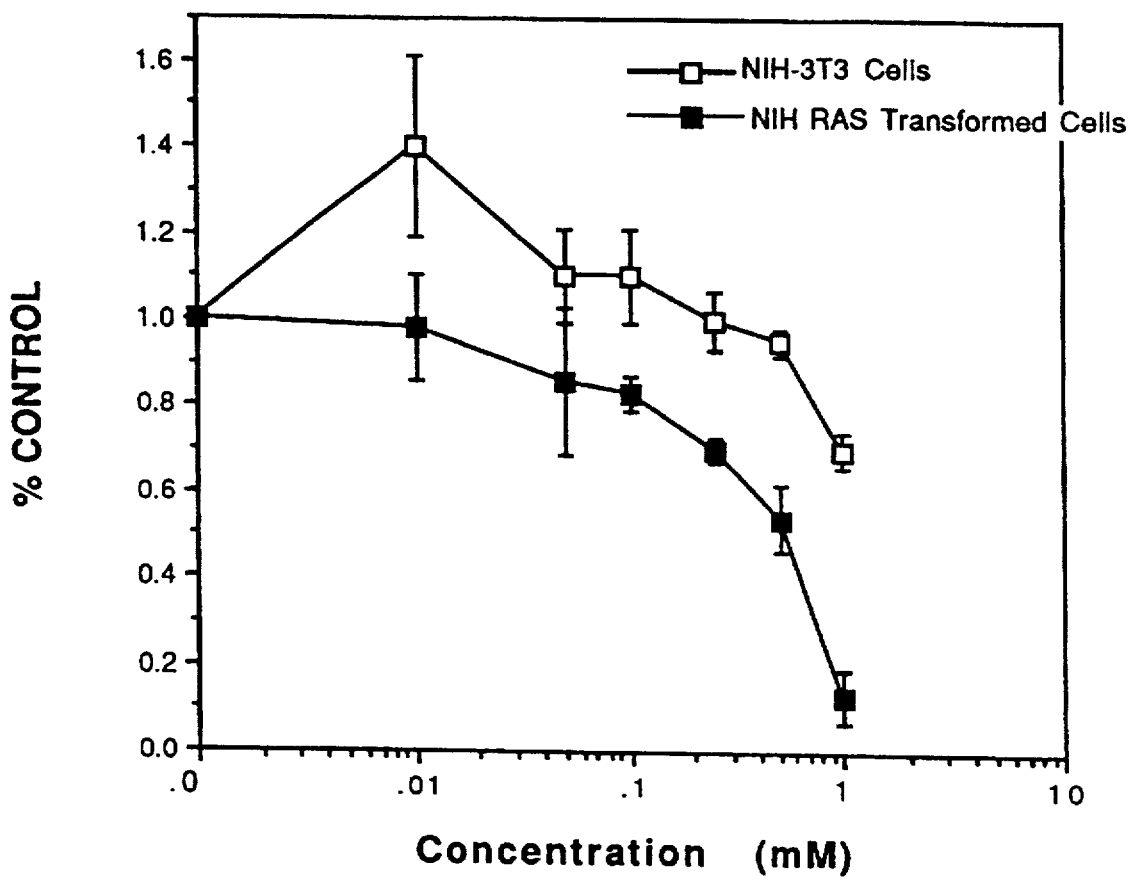
FIG. 4 shows CT1505 cytotoxicity on NIH-3T3 cells and their Ras transformed counterpart, NIH-3T3 Ras cells. The cells were treated with various concentrations of CT1505 (in the mM range on a log scale) and later stained for cell viability with a fluorescence stain. CT1505 is cytotoxic at higher concentrations, and thus shows antitumor activity.

This example illustrates that CT1505 has cytotoxic activity for NIH-3T3 and NIH-Ras transformed tumor cells. Cytotoxicity of the cells was determined with concentrations of CT1505 up to 1.0 mM (see FIG. 4). Cytotoxic activity was seen at drug concentrations over 0.1 mM.

EXAMPLE 6

Figure 5:
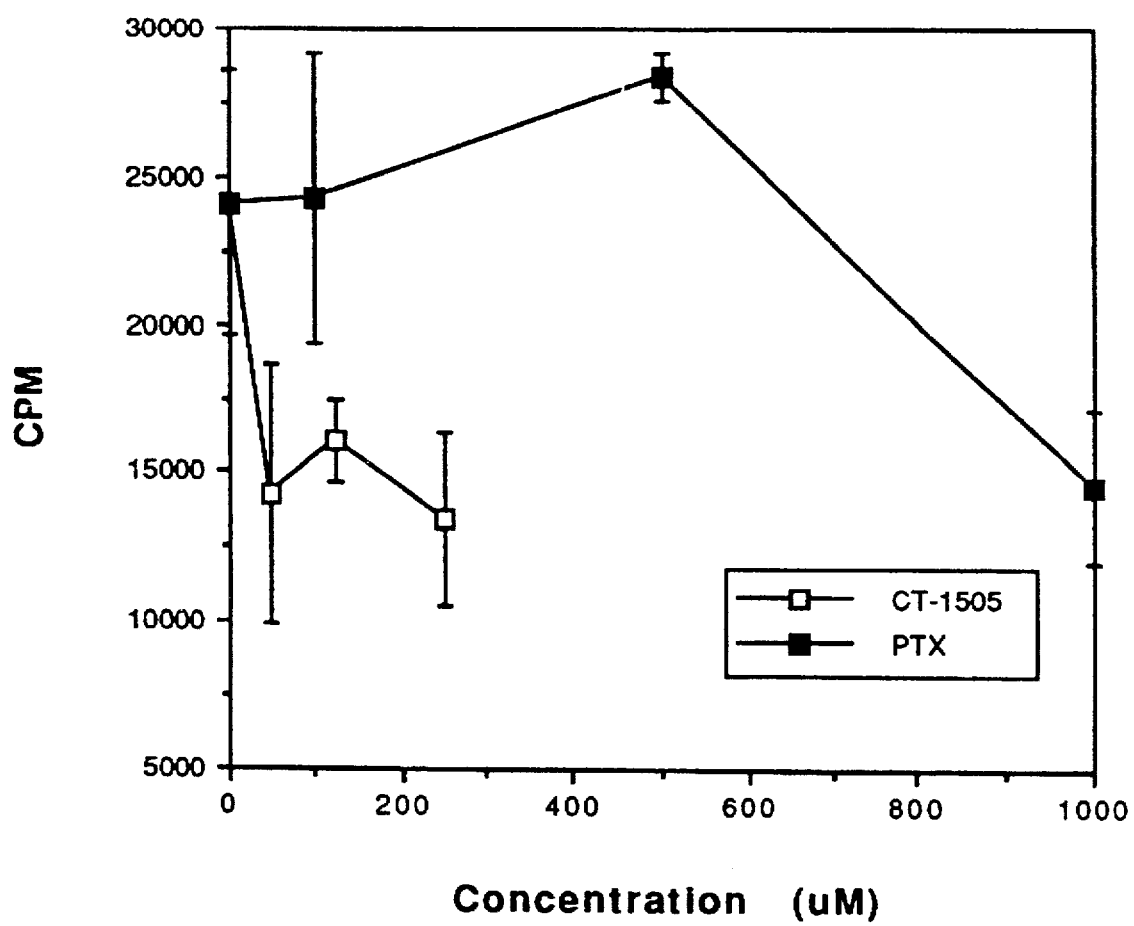
FIG. 5 shows a mixed lymphocyte reaction with CT1505 and PTX showing more potent immune modulating activity with CT1505 than with PTX.

This example illustrates a mixed lymphocyte reaction comparing immune modulating activity of CT1505 and PTX at varying drug concentrations (FIG. 5). Generally, CT1505 was a more potent drug for cause immune modulating activity than was PTX (FIG. 5).

We claim:

1. A pharmaceutical composition consisting essentially of 1-(5-oxohexyl)-3-methylxanthine, and an anti-P450 agent other than nifedipine in admixture with a pharmaceutically acceptable excipient.

2. The pharmaceutical composition of claim 1 wherein the anti-P-450 agent is a quinolone.

3. A method for treating inflammation in a subject in need of such treatment, comprising administering an effective amount of 1-(5-oxohexyl)-3-methylxanthine or a pharmaceutical composition thereof.

4. The pharmaceutical composition of claim 2 wherein the quinolone is selected from the group consisting of enoxacin, pefloxacin, and ciprofloxacin.

5. The pharmaceutical composition of claim 1 wherein the anti-P450 agent is selected from the group consisting of propranalol, metaprolol, verapamil, diltiazem, cimetidine, norfloxacin, ofloxacin, erythromycin, troleandomycin, ketoconizole, thiabenzadole, isoniazid, mexiletine, and dexamethasone.

* * * * *